(12) United States Patent
Burren et al.

(10) Patent No.: US 9,205,195 B2
(45) Date of Patent: Dec. 8, 2015

(54) DOSE SETTING DEVICE FOR AN INJECTION DEVICE

(75) Inventors: Stefan Burren, Schwarzenburg (CH); Jürg Hirschel, Bern (CH); Samuel Martinoia, Bern (CH); Ulrich Moser, Heimiswil (CH); Markus Tschirren, Kirchberg (CH)

(73) Assignee: TecPharma Licensing AG, Burgdorf (CH)

( * ) Notice: Subject to any disclaimer, the term of this patent is extended or adjusted under 35 U.S.C. 154(b) by 309 days.

(21) Appl. No.: 13/164,919

(22) Filed: Jun. 21, 2011

(65) Prior Publication Data

US 2011/0319835 A1    Dec. 29, 2011

Related U.S. Application Data

(63) Continuation of application No. PCT/EP2009/060998, filed on Aug. 26, 2009.

(30) Foreign Application Priority Data

Dec. 22, 2008    (WO) ................. PCT/EP2008/011019

(51) Int. Cl.
*A61M 5/315*    (2006.01)

(52) U.S. Cl.
CPC ........ *A61M 5/31541* (2013.01); *A61M 5/31551* (2013.01); *A61M 5/31585* (2013.01); *A61M 5/31558* (2013.01); *A61M 5/31575* (2013.01); *A61M 2005/3154* (2013.01)

(58) Field of Classification Search
CPC ..................... A61M 5/31525; A61M 5/31526; A61M 5/31528; A61M 5/3153; A61M 5/31533; A61M 5/31535; A61M 5/31536; A61M 5/3154; A61M 5/31545; A61M 2005/3154; A61M 5/31541; A61M 5/31573; A61M 5/31593
USPC .................................................. 604/207–211
See application file for complete search history.

(56) References Cited

U.S. PATENT DOCUMENTS

| | | | |
|---|---|---|---|
| 6,004,297 A | 12/1999 | Steenfeldt-Jensen et al. | |
| 7,811,263 B2 | 10/2010 | Burren et al. | |
| 7,867,202 B2 * | 1/2011 | Moser et al. | 604/209 |
| 2006/0153693 A1 | 7/2006 | Fiechter et al. | |
| 2006/0184117 A1 | 8/2006 | Knight et al. | |
| 2007/0016142 A1 | 1/2007 | Burren et al. | |
| 2008/0077095 A1 | 3/2008 | Kirchhofer | |

(Continued)

FOREIGN PATENT DOCUMENTS

| | | |
|---|---|---|
| DE | 10 2005 063311 | 8/2006 |
| EP | 1 541 185 | 6/2005 |

(Continued)

*Primary Examiner* — Bhisma Mehta
*Assistant Examiner* — Larry R Wilson
(74) *Attorney, Agent, or Firm* — Dorsey & Whitney LLP; Stuart R. Hemphill, Esq.

(57) ABSTRACT

A dosing device for an injection device, the dosing device including an actuating element for adjusting and/or dispensing a dose from the injection device, a thrust element for generating a forward movement for discharging a dose and a coupling to which the actuating element and the thrust element are coupled such that a rotational movement of the actuating element is transmitted directly to the thrust element and an axial movement of the actuating element is different than an axial movement of the thrust element.

11 Claims, 19 Drawing Sheets

(56) References Cited

U.S. PATENT DOCUMENTS

2008/0183138 A1 7/2008 Moser et al.
2008/0234634 A1* 9/2008 Eiland et al. .................. 604/208

FOREIGN PATENT DOCUMENTS

| WO | WO 2004/078240 | 9/2004 |
| WO | WO 2006/125329 | 11/2006 |

* cited by examiner

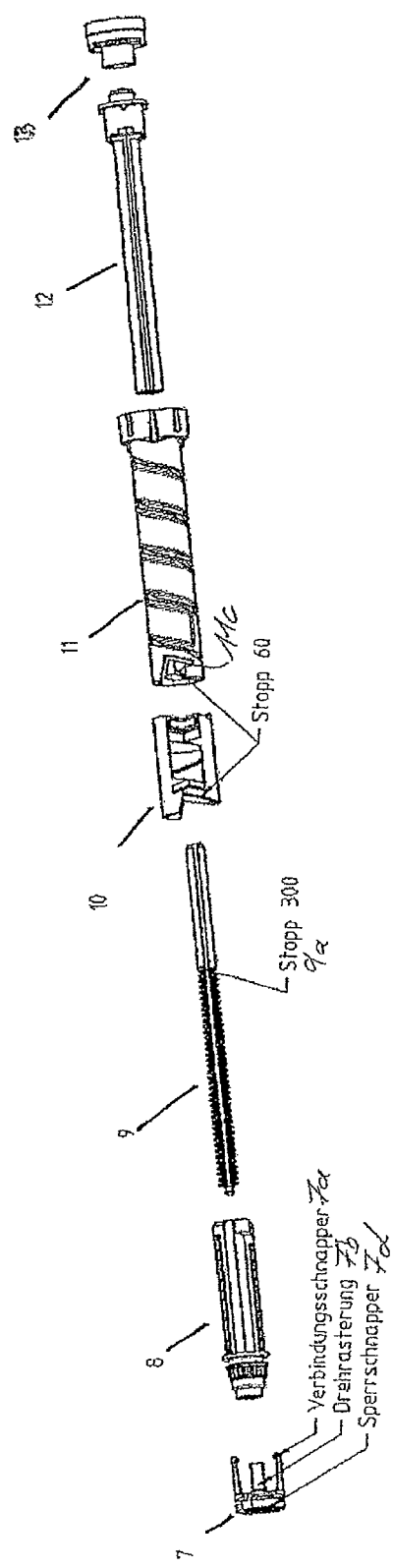

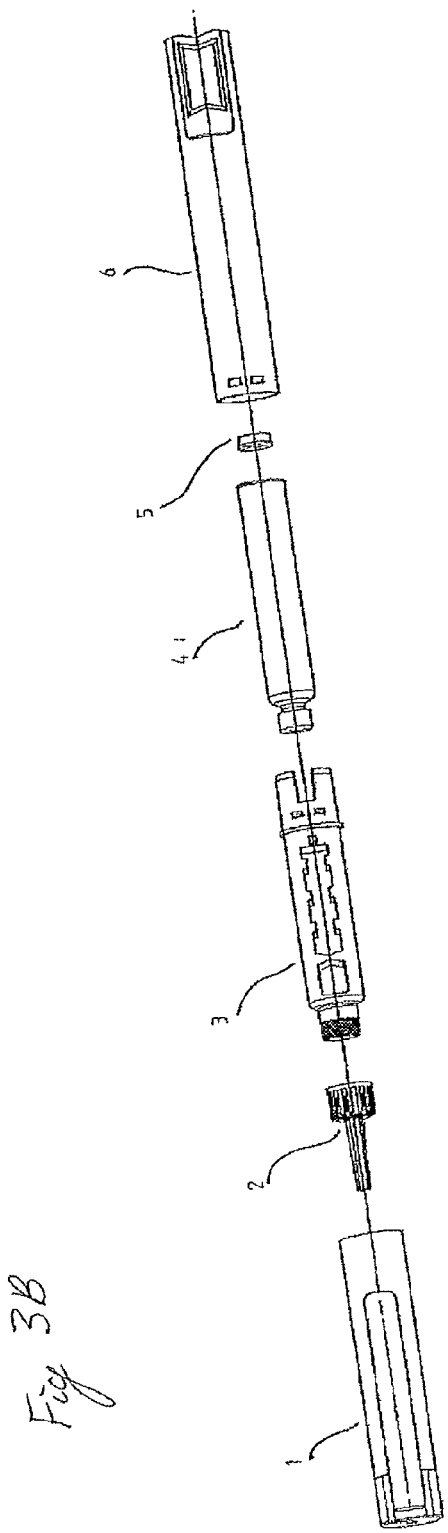

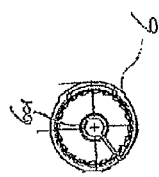
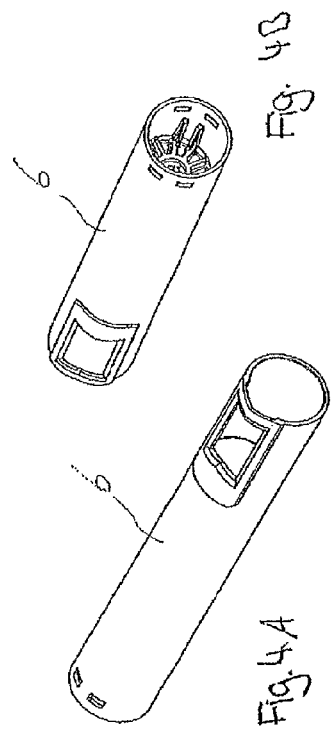
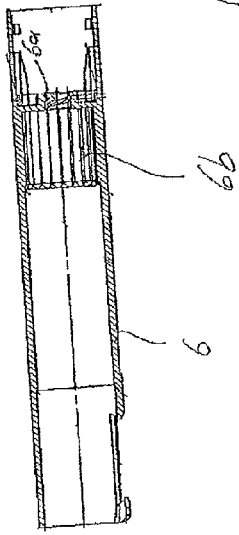

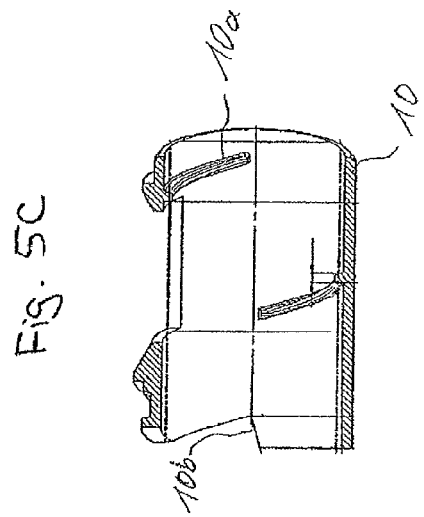
Fig. 5C
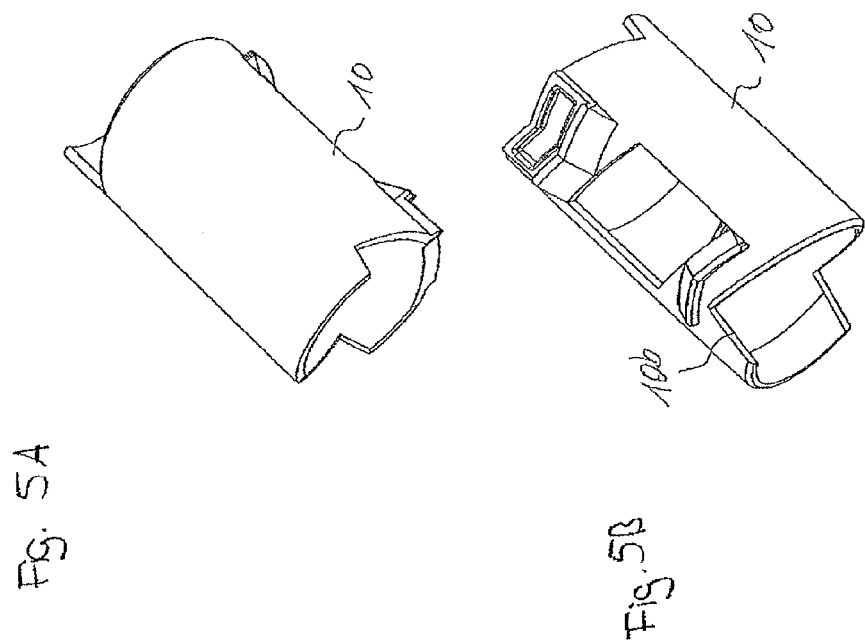
Fig. 5A
Fig. 5B

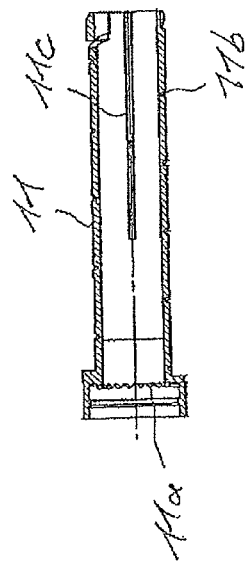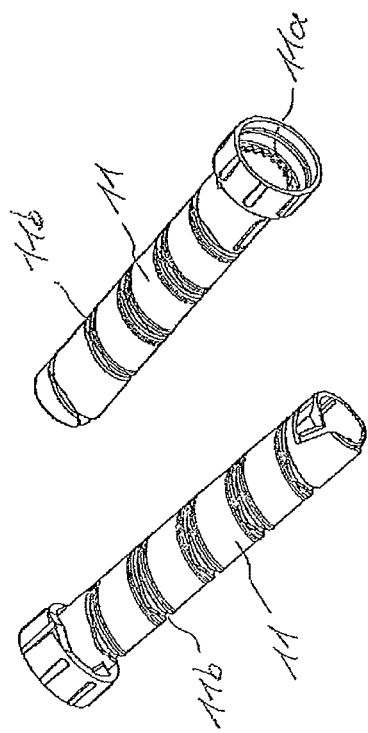

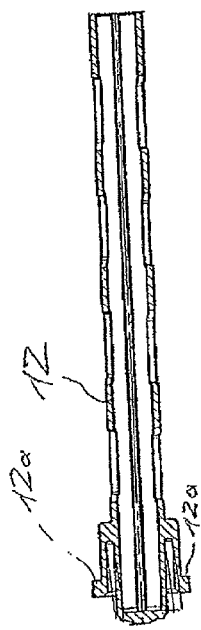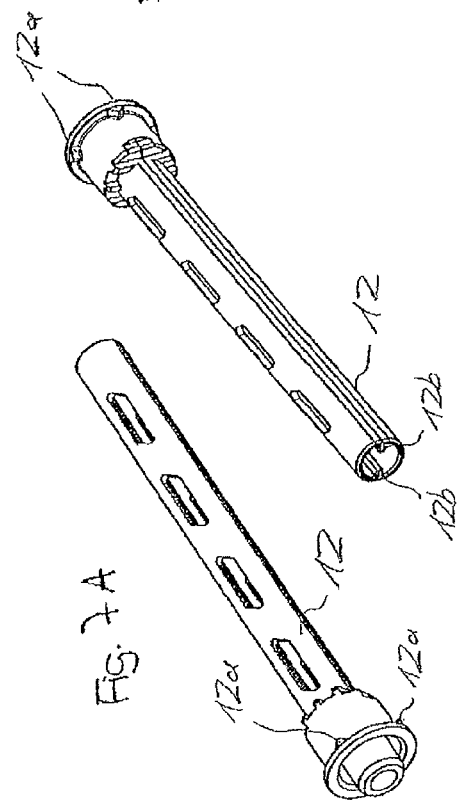

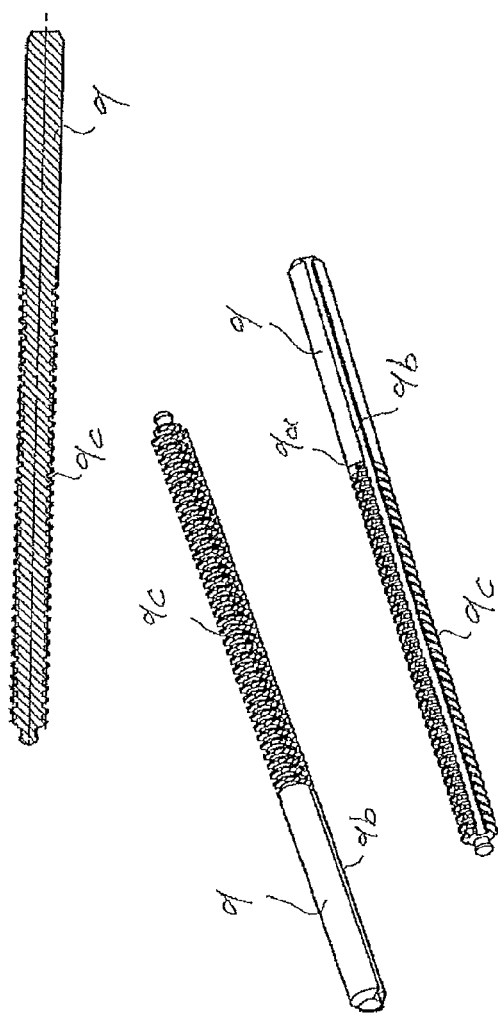

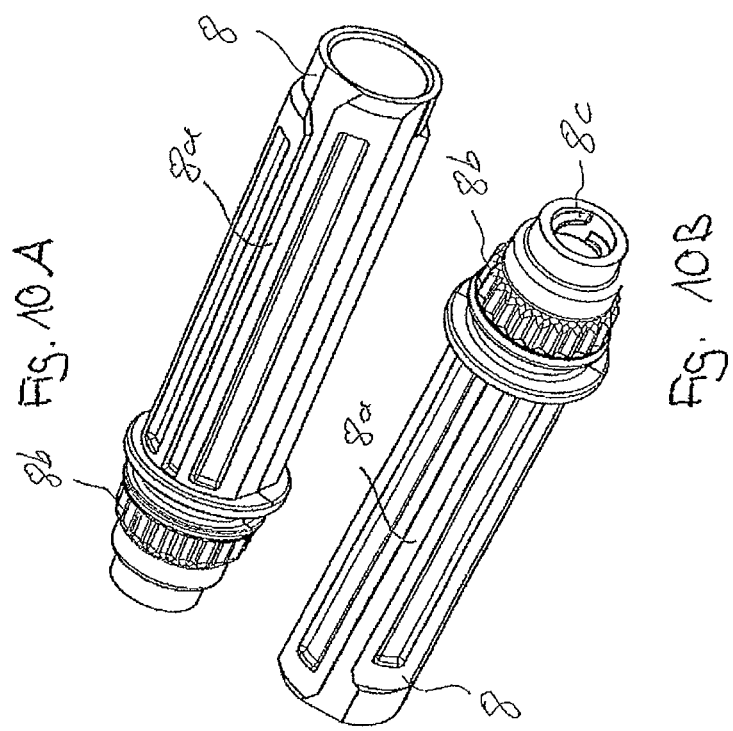
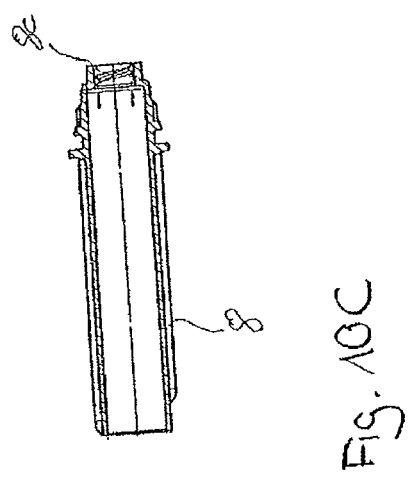

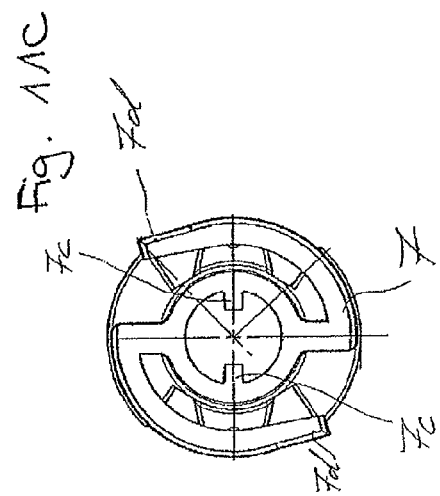
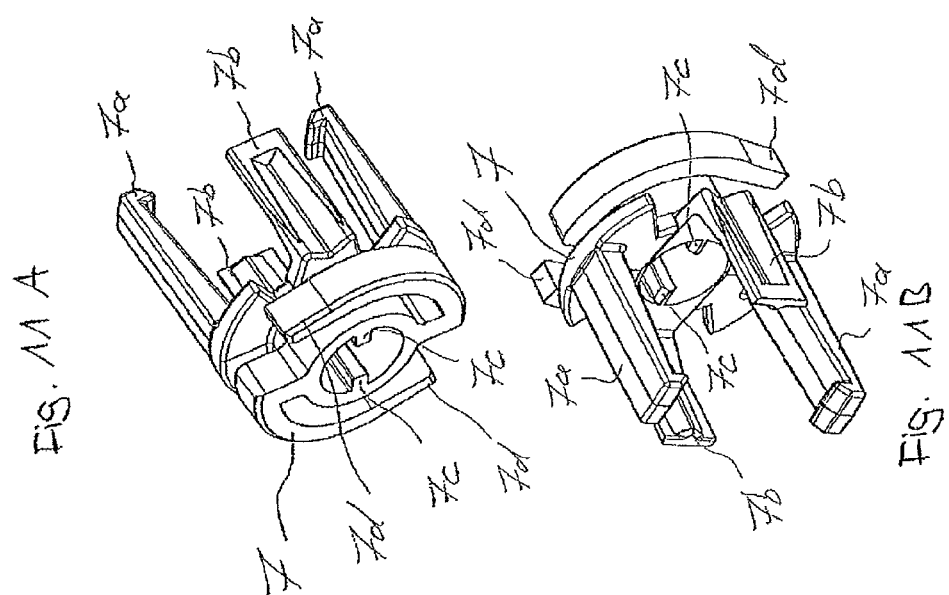

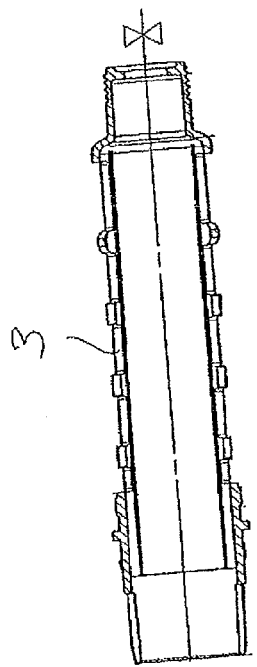
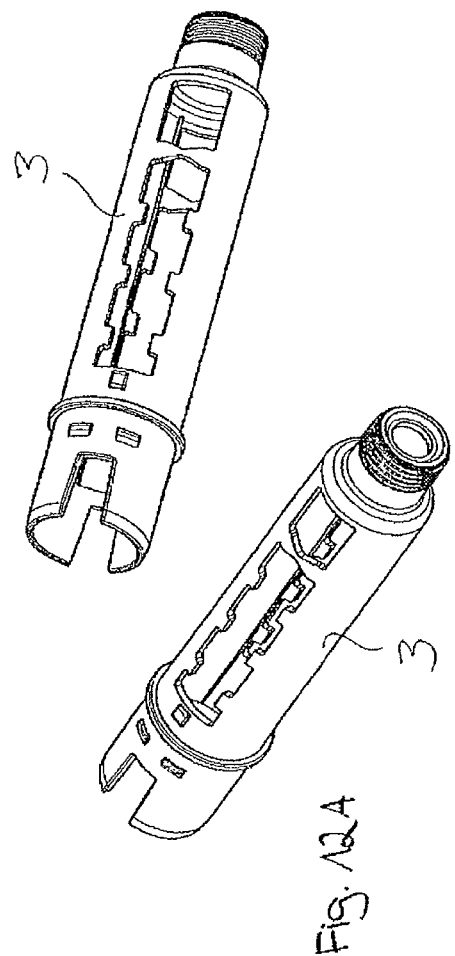
Fig. 12A
Fig. 12B
Fig. 12C

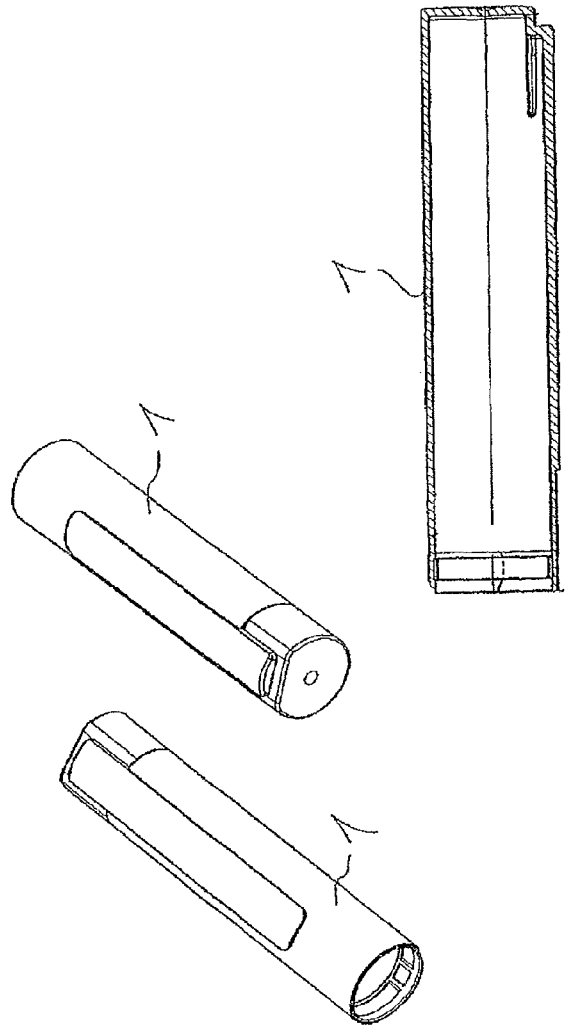

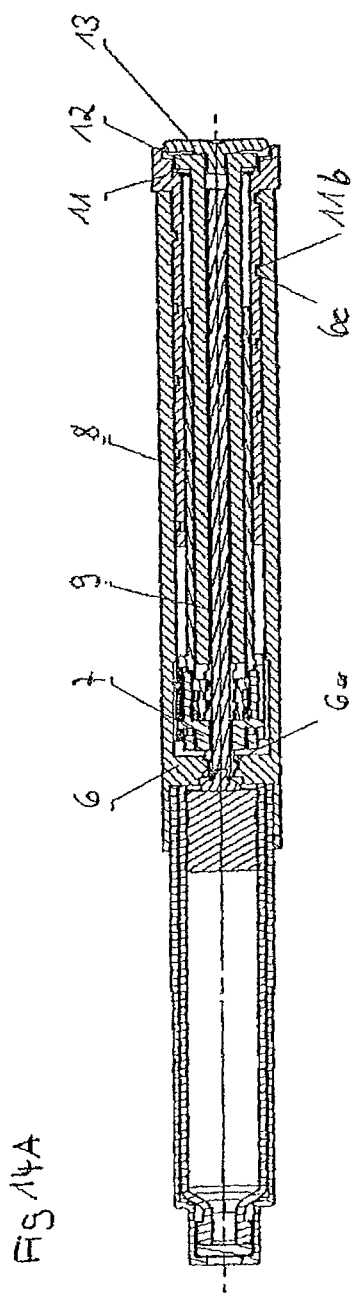

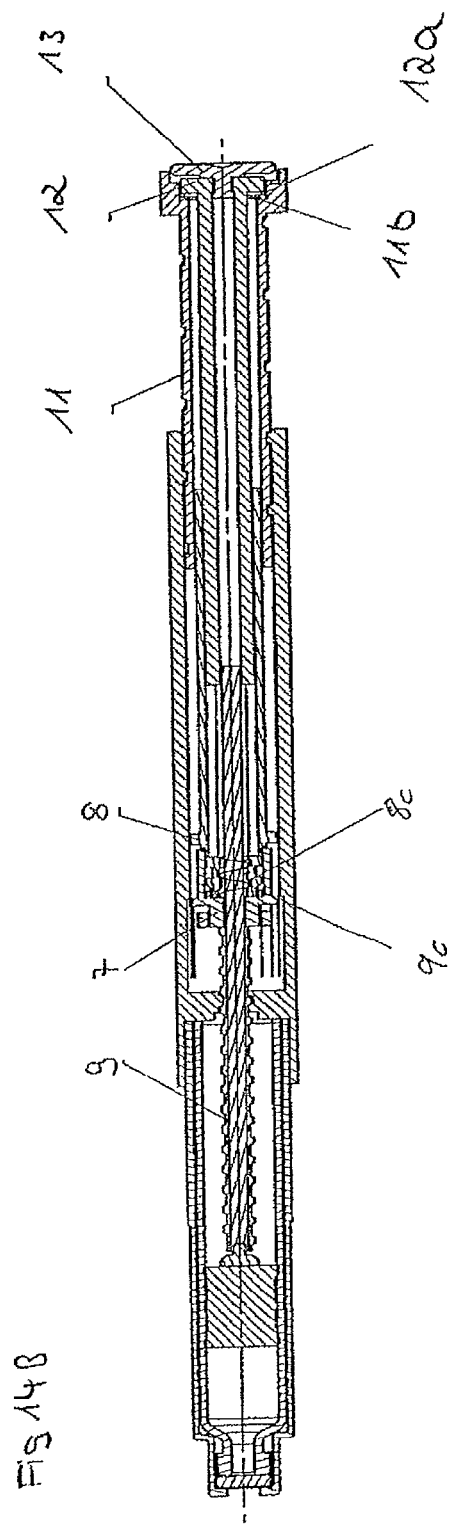

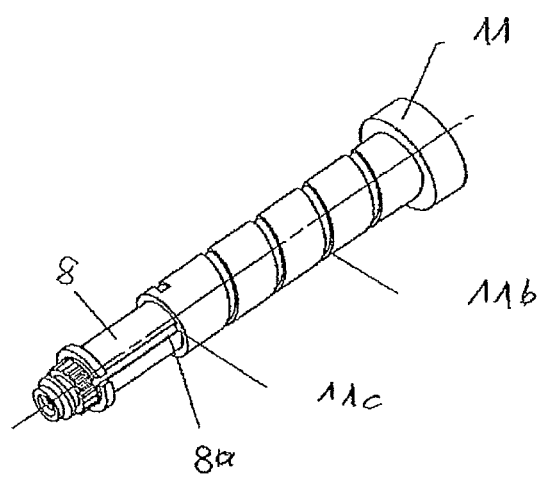

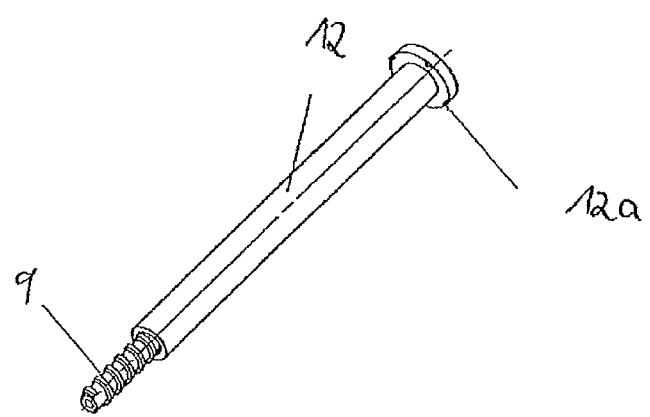

DOSE SETTING DEVICE FOR AN INJECTION DEVICE

CROSS-REFERENCED RELATED APPLICATIONS

This application is a continuation of International Patent Application No. PCT/EP2009/060998 filed Aug. 26, 2009, which claims priority to International Patent Application No. PCT/EP2008/011019 filed Dec. 22, 2008, the entire contents of each of which are incorporated herein by reference.

BACKGROUND

This application relates to devices for injecting, delivering, dispensing or infusing a substance, and to methods of making and using such devices. More particularly, it relates to a dose setting device for an injection device, more particularly a dose setting device by which a dose or quantity of a substance to be dispensed from or with the aid of an injection device can be set.

A dose setting device and an injection device are known from patent application WO 2006/125329 A1 owned and filed by the owner of the present application. For details of the structure of a dose setting device and an injection device, e.g. in accordance with the present application, reference may be made to the noted application (i.e. WO 2006/125329 A1), the entire disclosure and teaching of which is incorporated herein by reference.

SUMMARY

In one embodiment, the present invention comprises a dosing device or mechanism for an injection device, the dosing device comprising an actuating element for adjusting and/or dispensing a dose from the injection device, a thrust element for generating an axial movement for discharging a dose and a coupling to which the actuating element and the thrust element are coupled such that a rotational movement of the actuating element is transmitted directly to the thrust element and an axial movement of the actuating element is different than the axial movement of the thrust element.

In one embodiment, the present invention relates to a dosing device for an injection device, with an actuating element for adjusting and/or dispensing a dose from the injection device, a thrust element for generating a forward movement for discharging a dose, and a coupling to which the actuating element and the thrust element can be coupled such that a rotational movement or discharging movement of the actuating element is transmitted directly to the thrust element and an axial movement of the actuating element is greater than an axial movement of the thrust element. In some embodiments, the relative axial movements of the actuating and thrust elements may be referred to or thought of as being stepped down or stepped up.

In one embodiment, the present invention relates to a dose setting device for an injection device with an operating element, such as a rotating knob or rotating sleeve, guided in a dose setting element, in a housing of the injection device or in an insert which can be connected to or inserted in the housing so that it is fixed, e.g. prevented from rotating and/or from moving translationally. In some embodiments, the operating element is in threaded engagement with the dose setting element, housing or insert, and can be moved to set a dose to be dispensed from the injection device, e.g. screwed or turned out. In some embodiments, the operating or setting element may be screwed out of the dose setting device or injection device in the proximal (rearward) direction to set or select a dose, then fully rotated back or screwed in again to dispense the dose. A driving element, such as a plunger rod or threaded rod, is mounted in the dose setting device or injection device and is guided in an internal thread of the dose setting or injection device, for example in a housing internal thread disposed in a housing base. The driving element or threaded rod may have a flange at its distal (forward, front or leading) end which pushes against a stopper of an ampoule associated with and/or contained in the injection device and is able to push the stopper into the ampoule to force out a substance contained in the ampoule and thus dispense the substance from the injection device. Based on one aspect of the invention, the operating element and the driving element, for example a rotatable setting knob and a threaded rod, respectively, can be coupled and/or are coupled by a claw coupling during or before the dispensing operation. Thus, a dispensing movement of the operating element, e.g. a rotating movement, can be directly or immediately transmitted to the driving element. In this respect, the direct or immediate transmission may also take place via one or more inter-connected elements, e.g. such as those typically involved in mechanisms which may be referred to and/or thought of as couplings, joints, connections or transmissions. In some preferred embodiments, the operating element and driving element are coupled so that they rotate in unison, at least during a dispensing operation.

Directly and/or immediately transmitting a movement, e.g. a rotating movement, from an operating element to the driving element enables the dose setting element to operate with a high level of force. For example, in accordance with the present invention, it may not be necessary to transmit a rotating movement of the operating element to the driving element via one or more thread engagements first. In the case of a direct coupling, the operating element and driving element are connected to one another so that they rotate in unison and the ratio of the rotating movement is therefore not stepped up or down.

In some embodiments, the operating element is coupled with the driving element via a coupling element or a coupling unit. The coupling element may be provided in the form of a claw coupling, for example, and the coupling between the operating element and driving element is such that during the setting movement of the operating element, the operating element and driving element are uncoupled. Thus, the operating element can be freely rotated independently of the driving element in one direction to set a dose and in the opposite direction to correct the dose. Once a dose has been set and optionally corrected, the operating element is coupled with the driving element by the coupling element to permit a rotation in unison by moving it axially, for example. A pressure is applied to the coupling element in the axial direction, e.g. by pushing a knob provided on the proximal end of the injection device, so that the coupling element, which was previously uncoupled from the operating element, is coupled with the operating element to permit a rotation in unison. In some embodiments, the coupling element is coupled with the driving element or threaded rod to permit a rotation in unison by a web of the operating element locating in a longitudinal groove of the threaded rod (or vice versa). Consequently, once the coupling has been formed or locked, in other words when the coupling element has been joined, connected or coupled with the operating element, preventing a relative rotation, a rotating movement of the operating element can be transmitted, directly and without a thread disposed in between, to the coupling element, which is able to rotate together with the operating element due to the rotation-locking coupling. Thus, the rotating movement may be transmitted directly from the operating element to the driving element locked to the coupling element so as to rotate in unison with it.

Since the rotating movement is transmitted directly from the operating element to the driving element rotationally locked with or to the coupling element, the ratio of the axial movement can be stepped up or stepped down. For example, the thread by which the operating element is guided in the housing or a housing insert part of the injection device may have a different pitch from a thread, e.g. the external thread, of the driving element or threaded rod which is guided in a thread guide or an internal thread of the injection device or housing. If the thread pitch of the thread of the operating element, provided in the form of an external thread or internal thread (locating in an external thread integral with the housing for example), is greater than the thread pitch of the driving element or threaded rod, a step down in ratio can be obtained during a dispensing operation, i.e. an axial distance traveled by the operating element as it is turned back during dispensing is longer than a distance traveled by the driving element or threaded rod. This means, relatively speaking, a user has to apply a lesser force over a longer distance to move the driving element or threaded rod forward in the forward driving direction by a force that is stronger over a distance that is shorter.

In some preferred embodiments, the operating element and the driving element or threaded rod move in the same direction (the distal, dispensing, forward or delivery direction), at least during the dispensing operation. The thread in which the operating element is guided is one which is not retained by friction or not self-locking, so that the operating element can be easily pushed back or into the injection device due to a pressure acting in the axial direction applied by a user, thus causing the operating element to rotate and screw in without a user having to undertake a rotating movement during the dispensing operation. The threaded engagement of the driving element or threaded rod may be frictional or self-locking and/or non-self-locking or non-frictionally retained.

In some preferred embodiments, a knob or operating point at the distal end of the operating element may be provided. Such a feature may be rotatably guided inside the operating element, for example. Thus, a user can press the knob to apply a force to the operating element acting in the axial direction of the injection device, and the operating element is able to rotate relative to the knob held by the user as it is screwed in.

In some embodiments, the coupling element may be coupled with the operating element to rotate in unison with it and uncoupled from it again by a claw or other suitable joint or coupling. To this end, one or more tines and/or grooves may be provided on an annular or at least partially circumferentially extending surface on both the operating element and the coupling element, which lie opposite one another and which couple the driving element with the coupling element in a rotationally locked arrangement in the mutually meshing state and which enable a relative rotation between the driving element and coupling element in the non-meshing state. In some preferred embodiments, the claw coupling is designed so that the coupling is released in the absence of an axial force closing the coupling. In other words, the driving element and coupling element are able to rotate relative to one another if a user is not directly or indirectly applying any axial pressure to the coupling element in the distal direction, for example, via a knob connected to the coupling adjoining or lying in the vicinity of the coupling.

Another option would be for a coupling element to be locked to the operating element so as to rotate in unison with it, at least during a dispensing movement or permanently but not to be rotationally locked to and coupled with the driving element except during or before a dispensing operation.

In some embodiments, the coupling element may be a single part or may comprise several parts or coupling components or elements, provided the operating element can be uncoupled from the driving element and these elements are able to effect a relative rotating movement during the setting operation, and can be coupled in a rotationally locked arrangement before and/or during a dispensing or administering operation.

In some embodiments, a rotation or rotational lock is provided in the form of a known or suitable ratchet mechanism in the dose setting or injection device. Via the ratchet mechanism the driving element or the threaded rod can be rotationally locked relative to the dose setting or injection device at one end, i.e. the threaded rod is able to rotate relative to the dose setting or injection device in only one direction, whereas a rotation in the opposite direction is prevented by the lock. Thus, the threaded rod, guided in the dose setting or injection device by the thread, can be screwed into the injection device in the distal (or forward or driving) direction only.

In some embodiments, the threaded rod may be guided in a uni-directional rotation locking element, such as a ratchet part. A counter-rotation locking element may be coupled with the driving element or threaded rod in a rotationally locked arrangement by providing one or more projections or webs on the counter-rotation element, directed in the radial direction toward the driving element, which are able to locate or be received in axial longitudinal grooves or longitudinal ridges of the driving element or threaded rod. Another way of providing a rotation-locking coupling is by using projections on the threaded rod which locate in co-operating and/or complementary recesses of the counter-rotation lock or the counter-rotation locking element. The counter-rotation locking element may comprise one or more elements or arms biased radially outwardly, which co-operate with steps or circumferentially extending projections on the internal face of the injection device or a housing so that the arms are able to travel across the circumferentially extending steps on the internal face in one direction and snap in after moving past a step, thereby blocking or preventing a backward rotation.

In some embodiments, the lock element may be coupled with a unit or an element for fixing a maximum settable dose, e.g. snap-fitted on it. For example, the lock element may be coupled with such a stop element so that it is prevented from moving axially, in which case the stop element drives the lock element with it during a movement in the axial direction, thereby enabling a relative rotation. Clicking noises may be generated during this relative rotation, for example by elastic or resilient arms of the counter-rotation lock or lock element locating in co-operating teeth of the stop element or counter-rotation lock.

In some embodiments, a trigger knob is provided on the coupling element and/or on the operating element. The trigger knob may be mounted so that it is able to rotate, e.g. about its longitudinal axis relative to the coupling element. Accordingly, the trigger knob may be in the vicinity of the coupling mentioned above, in other words in the proximal (or rear) region of the injection device. A pressure applied to the trigger knob causes the coupling element to establish a coupling, thereby creating a rotation lock between the operating element and driving element or threaded rod. Continuing to apply pressure to the trigger knob will cause the operating element together with the threaded rod to be pushed in the distal (forward or delivery) direction into the injection device and a relative rotation takes place between the rotatably mounted trigger knob on the one hand and the operating element and driving element on the other hand.

In some embodiments, the present invention relates to and/or comprises an injection device incorporating a dose setting device of the type described above.

In some embodiments, as part of a method of setting and administering a dose from an injection device, an operating and/or setting element is uncoupled from a driving element during the process of setting a dose, at least as far as transmitting a rotating movement is concerned, so that a dose can be set by rotating the operating element and can optionally also be corrected by a counter-rotation. Before or during the process of dispensing a dose, the operating element is coupled with the driving element in a rotationally locked arrangement, for example by a coupling element or a coupling, so that a rotating movement of the operating element guided in a thread in a dose setting device or injection device can be transmitted directly as a rotating movement to the driving element or a threaded rod. As this happens, the ratio of the rotating movement of the operating element is not stepped up or down, which means that the operating element and driving element rotate together by the same angle due to the rotation-locking coupling.

In some embodiments, the present invention relates to a dose setting device for an injection device with a dose-restricting element, which also may be referred to and/or thought of as a restrictor or compensating element, which is able to limit the setting of a maximum total dose to be set and which is coupled with a setting or priming element so that a setting or priming movement of the setting element leads to or is converted into a movement of the compensating or restrictor element in the proximal (rearward) or distal (forward) direction of the injection device. Since the compensating or restrictor element moves in the same direction as the threaded rod or plunger rod during the process of dispensing a dose, the length of the injection device can be made shorter, even if the compensating or restrictor element is guided directly on the plunger rod or threaded rod.

In some embodiments, upon reaching a maximum settable dose or the maximum dose to be dispensed from the injection device, the compensating or restrictor element moves into contact with and/or lodges against a restriction or a stop, for example an axial or radial stop, to prevent the restrictor element from being moved any farther. The stop may be provided in the form of an end of a thread of a threaded rod and/or an axial and/or radial stop on the threaded rod, on the housing of the injection device or on another component.

In some preferred embodiments, the restrictor element is coupled with the setting element so that a movement of the setting element is no longer possible in a priming direction when the restrictor element is against the restrictor stop. However, a counter-rotation may be possible. For example, the setting and restrictor element may be coupled in a rotationally locked arrangement, at least when setting a dose.

In some embodiments, the present invention comprises an injection device incorporating a dose setting device of the type described above, e.g. with a restrictor element.

In some embodiments, the present invention relates to a method of restricting a maximum dose which can be set on an injection device, the method involving a restrictor element coupled with a setting element so that the restrictor element moves toward a restriction or a stop when the setting element is moved. In some embodiments, the coupling between the restrictor element and setting element is designed so that the setting element can no longer be moved in a priming or setting direction, for example proximally out of the injection device, when the restrictor element is lying against the restriction or the stop.

In some embodiments, the present invention comprises a dose setting device for an injection device for restricting or limiting a maximum settable total dose. Accordingly, the dose setting device comprises a restrictor element, which is coupled with a rotatable and/or slidable setting element and is rotationally locked so that the restrictor element is moved toward a restriction or a stop as the setting element moves, and is moved back to its initial position relative to the dose setting device or injection device when the set dose has been dispensed, for example by moving the setting element back. In some preferred embodiments, the restrictor element moves between two positions and thus effects what may be thought of and/or referred to as a "pendulum movement." In this regard, wherein the stop or the restriction element moves in the direction toward the limiting element only while the dose is being set and/or only when the dose is being dispensed, the distance or gap between the limiting element and the stop causing the actual restriction or lock, which may be provided on an axially sliding threaded rod for example, becomes shorter every time a dose is dispensed. Thus, the maximum total dose to be set after the previously dispensed dose is reduced.

BRIEF DESCRIPTION OF THE DRAWINGS

FIG. 3 is an exploded diagram of the injection device illustrated in FIG. 1;

FIG. 4 depicts a housing of the injection device;

FIG. 5 illustrates a threaded sleeve of the injection device;

FIG. 6 illustrates a dose setting sleeve of the injection device;

FIG. 7 illustrates a coupling element of the injection device;

FIG. 9 illustrates a threaded rod of the injection device;

FIG. 10 illustrates a restrictor sleeve or restrictor nut of the injection device;

FIG. 11 illustrates a counter-rotation lock of the injection device;

FIG. 12 illustrates a carpoule or ampoule sleeve of the injection device;

FIG. 13 illustrates a protective cap of the injection device;

FIG. 14A is a sectional view illustrating another embodiment of an injection device in accordance with the present application in an as-sold state;

FIG. 14B shows the injection device illustrated in FIG. 14A in a primed state after dispensing a dose;

FIG. 14C illustrates a coupling between a setting element and restrictor element;

FIG. 14D illustrates how a threaded rod is guided in a coupling element;

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1:
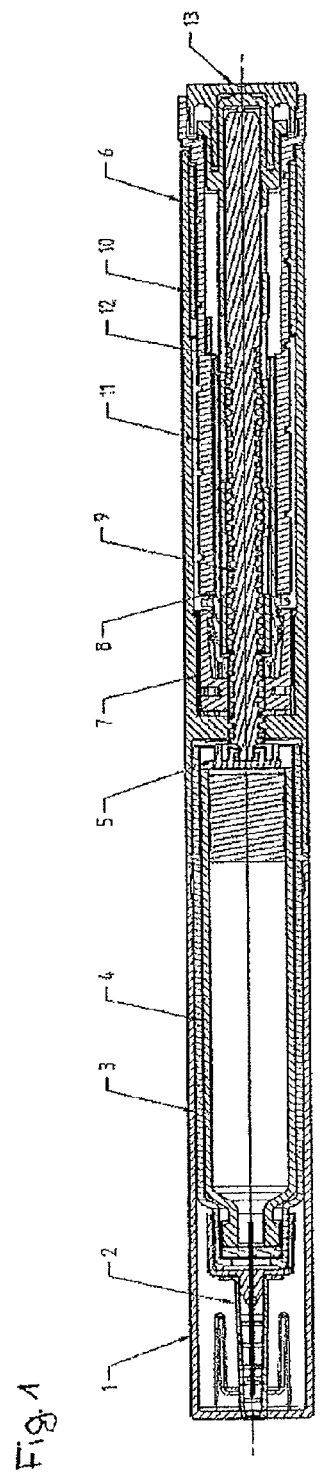
FIG. 1 is a cross-section of one embodiment of an injection device in accordance with the present application.
Figure 2:
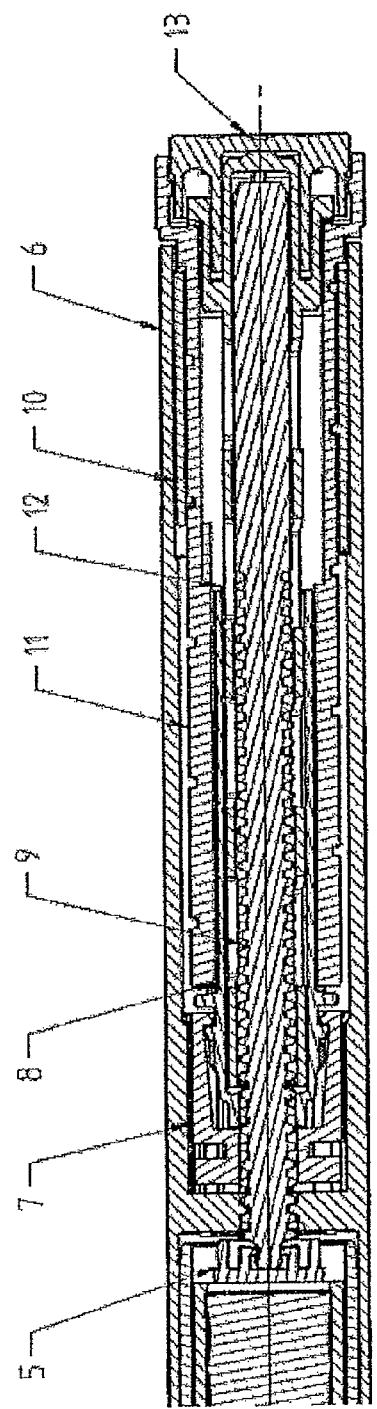
FIG. 2 is a detail of the dose setting and dispensing mechanism illustrated in FIG. 1.

As illustrated in FIGS. 1 to 3, an injection device or injection pen in accordance with the present application comprises a dose setting mechanism, a flange 5, a carpoule or ampoule 4 containing medicament, a carpoule holder 3, a needle 2 and a protective cap 1.

The flange 5 is snapped onto a threaded rod 9, which extends out of the dose setting mechanism. The carpoule 4 is retrained between the carpoule holder 3 and a housing 6 of the dose setting mechanism, which snap fit one in the other. As will be described in further detail below, in some embodiments, the dose setting mechanism comprises a mechanism for increasing the ratio of the force, restrictor elements and coupling elements.

The mechanism for increasing the ratio of the force comprises a threaded sleeve 10 (FIG. 5) locked in the housing 6 (FIG. 4) in a thread 10a in which runs or travels an operating element 11 (FIG. 6) which can be screwed out, which rotates a threaded rod 9 (FIG. 9) running in the thread of the housing 6 via the coupling 12 (FIG. 7).

Figure 8C:
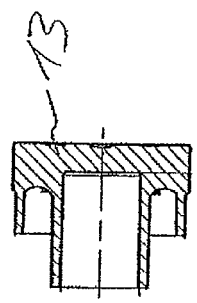
FIG. 8 illustrates a dose setting knob of the injection device.
Figure 8B:
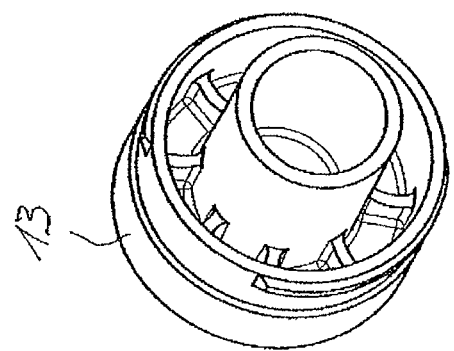
Figure 8A:
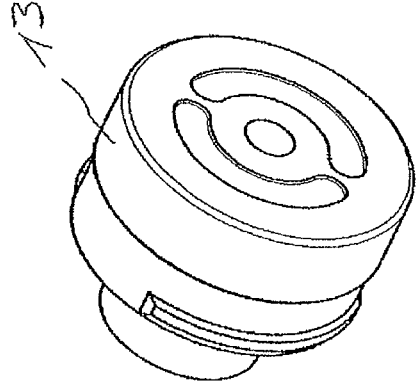

The coupling elements comprise a coupling 12 linearly guided on the threaded rod 9, the teeth 12a of which are able to mesh with teeth 11a of the operating element 11, and a dose setting knob 13 (FIG. 8) which absorbs the force applied by the user and transmits it to the coupling 12.

The restrictor elements comprise a restrictor sleeve 8 (FIG. 10) which constitutes a maximum dose restriction or restrictor 300 in conjunction with the thread end 9a of the threaded rod 9, and a counter-rotation lock 7 (FIG. 11) which prevents the threaded rod 9 from being rotated in one direction relative to the housing 6. It snaps axially with the restrictor sleeve 8 by snappers 7a and in conjunction with it constitutes a radial dose clicking mechanism including, in part, arms 7b.

FIG. 1 illustrates an embodiment of a dose setting device in accordance with the present application, whereby the dose setting function, in other words the movement by which the outwardly rotated operating element 11 is pushed in as the dose is being primed, is transmitted by a rotating movement of the coupling 12 which is coupled, after priming, directly to the threaded rod 9.

Accordingly, the embodiment of FIG. 1 may be referred to and/or thought of as a rotating pen. In other words, an axial movement is converted into a rotating movement and transformed back again. The operating element 11 does not apply force directly to the threaded rod 9.

The threaded rod 9 is locked to the housing 6 so as to rotate in unison with it by a uni-directional or one-way ratchet coupling 7. The ratchet coupling 7 is locked to the threaded rod 9 to rotate in unison with it via a key-groove connection 7c, 9b. Consequently, the threaded rod 9 can only screw or turn forward in the distal (forward) direction, guided by a thread 6a of the housing 6.

The operating element 11 is guided by an external thread 11b in an internal thread 10a of the threaded sleeve 10 secured to the housing or of the housing 6. When the dose is being primed, the operating element 11 is rotated out of the housing 6, wherein the operating element 11 moves axially and in the direction of rotation relative to the threaded rod 9 retained in the housing 6.

A restrictor nut 8 is locked to prevent any rotation relative to the setting or operating element 11. The nut 8 is locked by a groove 8a extending in the axial direction in which an axially extending web 11c of the operating element 11 locates, but is able to move axially relative to it.

During a rotating movement of the operating element 11, the restrictor nut 8 rotationally locked to the operating element 11 is rotated with it. The threaded rod 9 is locked in the housing 6 by the ratchet coupling 7 to prevent a rotation when the dose is being primed or the operating element 11 is being screwed out. As a result, the restrictor nut 8 screws on the threaded rod 9 in the proximal direction.

Before the start of the dispensing movement, the threaded rod 9 is coupled with the rotating element 11 in a rotationally locked arrangement. However, the operating element 11 and threaded rod 9 are able to move axially relative to one another. An element guided externally to the threaded rod 9 is provided as coupling 12, which is rotationally locked to the threaded rod 9 by a key-groove 9b, 12b. Disposed on the operating element 11 at the end face are circumferentially extending crowns 11a pointing in the proximal direction, which are able to mesh in oppositely lying claws 12a of the coupling element 12 at the end face pointing in the distal direction. As the operating element 11 is rotated out, the operating element 11 is able to move relative to the coupling element 12 because there is no force acting on the coupling element 12 in the distal direction. The claws 12a and crowns 11a run or slip past one another during the rotating movement of the operating element 11. As the dose is being primed, the coupling element 12 is prevented from rotating in the housing 6 due to the rotation-lock of the threaded rod 9, which is locked by a unilateral ratchet coupling 7 so that it cannot rotate relative to the housing 6.

During triggering, a force is applied to the coupling element 12 in the distal direction via the push knob 13 snap-fitted onto the coupling element 12 so that the coupling 12 is locked to prevent it from rotating relative to the operating element 11 due to the mutually meshing crowns 11a and claws 12a. The operating element 11 rotates during the pushing-in movement due to the thread guide (formed by elements 11 b, 10a) in the internal thread inside the housing 6. Since the operating element 11 is locked so as to rotate in unison with the coupling element 12, the rotating movement of the operating element 11 is transmitted to the threaded rod 9 which is rotationally locked to the coupling 12. The threaded rod 9 therefore rotates and is screwed inwardly in the distal (forward or dispensing) direction, guided by the internal thread 6a of the housing 6.

The restrictor nut 8 runs or travels on the threaded rod 9 and has an internal thread 8c in which the external thread 9c of the threaded rod 9 locates or is received.

The restrictor nut 8 may be screwed in the proximal (rearward) direction relative to the threaded rod 9, but only during the dose setting operation. During the dispensing operation, the restrictor nut 8 remains in the same position relative to the threaded rod 9 because the operating element 11 and threaded rod 9 are locked by the coupling 12 to rotate in unison and is moved back into its initial position together with the threaded rod 9. Consequently, the restrictor nut 8 is moved back to the same position in the pen (in what may be thought of and/or referred to as a pendulum movement) after the priming and dispensing movement. However, the position on the threaded rod 9 changed during the priming operation. The restrictor nut 8 is moved in the proximal direction relative to the threaded rod 9 during priming. The restrictor function of the restrictor nut 8 is achieved by a stop 9a on the threaded rod 9, which prevents the operating element 11 from being screwed farther out during priming when the restrictor nut 8 is lying against the stop.

Only the threaded rod 9 travels across a predefined maximum distance defined by the initial axial position of the restrictor nut 8 on the threaded rod 9, e.g. the axial distance from the initial axial position of the restrictor nut 8 to a threaded rod stop, which corresponds to the total quantity of medicament to be administered from the ampoule, for example 300 units. The same is not true of the restrictor nut 8, which effects the pendulum movement inside the pen.

Due to this design of the restrictor nut 8, the restrictor function can already be assured during priming of the dose because in the case of the last administered dose, the restrictor nut 8 is already in abutment with the stop 9a of the threaded rod 9 and blocks any further increase in dose or outward screwing of the operating element 11.

The threaded rod 9 has a lock to prevent a counter-rotation relative to the housing 6 in the form of a uni-directional coupling or counter-rotation lock 7. The counter-rotation lock 7 is axially coupled with the pendulum restrictor 8 by a snapper hook 7a.

The pendulum restrictor 8 and counter-rotation lock 7 can be rotated relative to one another via a dose clicking mechanism, created by the arms 7b passing across the teeth 8b of the restrictor nut 8.

Since functions, such as restricting the dose and locking a counter-rotation, are integrated inside the injection device, the setting element, respectively the dose setting knob of the operating element 11 and the trigger knob 13 retained in the coupling element 8, may be kept relatively flat, i.e. the height of the dose setting knob can be reduced, as a result of which the stroke movement needed by a patient's thumb to inject a set dose may be reduced.

During dispensing, the pendulum restrictor 8 and counter-rotation lock 7 are coupled and thus rotate in unison so that there are no clicking noises.

The counter-rotation lock 7 has snappers 7d biased radially outwardly, which locate in catches 6b of the circumferentially extending housing 6. During dispensing, the counter-rotation lock 7 rotates relative to the housing 6 and is therefore able to generate clicking noises. When the dose is being set or the dose is being corrected, the counter-rotation lock 7 is secured to the housing and therefore generates no clicking noises.

During clicking, apart from generating a noise, a tactile feedback may be generated for a user.

A stop 11c of the operating element 11 and a stop 10b of the threaded sleeve 10 restrict the maximum settable individual dose (these elements may be thought of and/or referred to as a restrictor 60).

FIG. 14A illustrates a dose setting device of an injection device based on a another embodiment, where the dose setting function, i.e. the inward movement of the operating element 11 screwed out (see FIG. 14B) during the process of setting the dose, is achieved by a rotating movement of the coupling 12, which is coupled once the dose has been set, transmitted directly to the threaded rod 9.

In accordance with some embodiments of the present invention, it is possible to obtain an increase in ratio and/or a decrease in ratio between a setting or dose setting element 11 and a driving element 9, for example when the dose is being set and/or when the dose is being administered.

The threaded rod 9 is locked to prevent a counter-rotation, for example by a ratchet coupling 7. The ratchet coupling 7 may be mounted on or carried by the housing 6. The ratchet coupling 7 is locked to rotate in unison with the threaded rod 9 by a key-groove or other suitable connection. In another embodiment, the ratchet coupling 7 may also be provided with an additional thread running in the opposite direction on the threaded rod 9. The threaded rod 9 can therefore only be screwed or turned forward in the distal direction, guided by the thread 6a of the housing 6.

The operating element 11 is guided in an internal thread 6c of the housing 6 by an external thread 11b. When setting the dose, the operating element 11 is screwed or turned out of the housing 6, as illustrated in FIG. 14B, wherein the operating element 11 moves axially and in the direction of rotation relative to the threaded rod 9 retained in the housing 6.

A restrictor nut 8 is locked or fixed so that it cannot rotate relative to the setting or operating element 11, for example by a web or projection 11c on the internal face of the operating element 11. The web 11c extends in the axial direction, illustrated in FIG. 14C, and is received in or locates in an axially extending groove 8a of the restrictor nut 8. The restrictor nut 8 travels on the threaded rod 9 and has an internal thread 8c in which the external thread 9c of the threaded rod 9 locates.

During a rotating movement of the operating element 11, the restrictor nut 8 rotationally locked to the operating element 11. The threaded rod 9 is locked to prevent rotation in the housing 6 when priming the dose or screwing out the operating element 11. As a result, the restrictor nut 8 is screwed on the threaded rod 9 in the proximal direction.

Figure 14E:
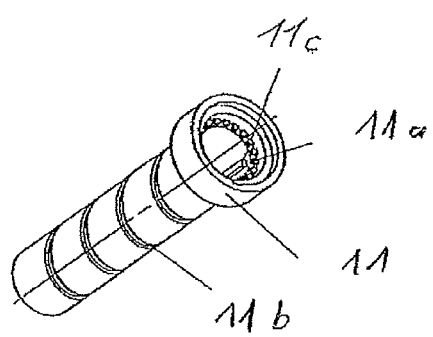
FIG. 14E is a perspective view of the setting or operating element.

Before the start of the dispensing movement, the threaded rod 9 is coupled with the operating element 11 to prevent a relative rotation. However, the operating element 11 and threaded rod 9 are able to move axially relative to one another. An element guided externally to the threaded rod 9 is provided as the coupling 12, as illustrated in FIG. 14D, which is locked by a positive connection to the threaded rod 9 to rotate in unison with it. Crowns or claws 11a are provided on the operating element 11 at the end, pointing in the proximal direction, as illustrated in FIG. 14E, which are able to mesh with oppositely lying circumferentially extending crowns or claws 12a at the end of the coupling element 12 pointing in the distal direction. As the operating element 11 is being screwed out, the operating element 11 is able to rotate relative to the coupling element 12 because no force acts on the coupling element 12 in the distal direction. The claws 11a and 12a run or slide past one another during the rotating movement of the operating element 11. When the dose is being primed, the coupling element 12 is locked to prevent rotation in the housing 6 due to the rotation-lock inside the threaded rod 9, which is locked to prevent rotation in the housing 6, e.g. by a ratchet mechanism.

During triggering, a pressure is applied, via a trigger knob 13, to the coupling or coupling element 12 in the distal direction so that the coupling or coupling element 12 is locked to rotate in unison with the operating element 11 due to the mutually meshing crowns or claws 11a and 12a. As it is pushed in, the operating element 11 rotates due to the guiding action of the thread in the internal thread 6c inside the housing 6. Due to the fact that the operating element 11 is locked to rotate in unison with the coupling or coupling element 12, the rotating movement of the operating element 11 is transmitted to the threaded rod 9 rotationally locked to the coupling or coupling element 12. The threaded rod 9 therefore rotates and is screwed or turned inwardly in the distal direction, guided by the internal thread 6a of the housing 6.

The restrictor nut 8 screws or moves in the proximal direction relative to the threaded rod 9 only when the dose is being primed. During dispensing, the restrictor nut 8 remains in the same position relative to the threaded rod 9 because the operating element 11 and the threaded rod 9 are locked in rotation by the coupling element 12, and is moved back into its initial position with the threaded rod 9. Consequently, the restrictor nut 8 is moved back to the same position (in what may be thought of and/or referred to as a pendulum movement) in the pen after the priming and dispensing movement. However, the position on the threaded rod 9 changed during priming. The restrictor nut 8 is moved in the proximal direction relative to the threaded rod 9 during priming. The restrictor function of the restrictor nut 8 is achieved by a stop (axial or in the circumferential direction) on the threaded rod 9. This prevents the operating element 11 from being screwed out farther once the restrictor nut 8 is lying against the stop when the dose is being set.

FIG. 14B illustrates a state in which the restrictor nut 8 has reached the thread end of the threaded rod 9 and can therefore be turned no farther, so that a further increase in the dose or outward screwing of the operating element 11 is not possible.

In this embodiment, the threaded rod 9 travels a predefined maximum distance, defined by the initial axial position of the restrictor nut 8 on the threaded rod 9, e.g. the axial distance from the initial axial position of the restrictor nut 8 to a threaded rod stop, which corresponds to the total quantity of medicament to be dispensed from the ampoule, e.g. 300 units. The same is not true of the restrictor nut 8, which effects a pendulum movement inside the pen.

As a result of this design of the restrictor nut 8, the restrictor function can be assured during the priming operation because in the case of the last dose to be dispensed, the restrictor nut 8 is already lying against the stop of the threaded rod 9 and blocks another increase in the dose or outward screwing of the operating element 11.

Figure 14F:
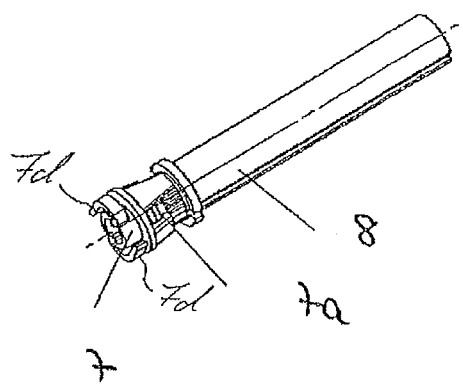
FIG. 14F illustrates how a counter-rotation lock is coupled with the pendulum restrictor.

The threaded rod 9 has a lock to prevent a counter-rotation relative to the housing 6. The lock may be provided in the form of a known or suitable uni-directional or one-way coupling 7. The counter-rotation lock is axially coupled with the pendulum restrictor 8 in FIG. 14F, e.g. with a snapper hook 7a. The pendulum restrictor 8 and counter-rotation lock 7 are able to rotate freely relative to one another.

Again, since functions such as restricting the dose and preventing a counter-rotation are integrated inside the injection device, the setting element (which may be thought of and/or referred to as comprising the dose setting knob or the proximal part of the operating element 11 and the trigger knob 7 retained in the coupling element 12), may be of a relatively flat design, in other words the height of the dose setting knob can be reduced, as a result of which the stroke movement needed by a patient's thumb to inject a set dose can be reduced.

In one embodiment, a clicking or noise-producing element may be disposed between the pendulum restrictor 8 and the counter-rotation lock 7, e.g. a snapper biased radially outwardly from the pendulum restrictor 8 locates in catch elements of the circumferentially extending counter-rotation lock 7 or vice versa. During dispensing, the pendulum restrictor 8 and counter-rotation lock 7 are coupled and thus rotate in unison, so that no clicking noises are generated.

The counter-rotation lock 7 has snappers 7d biased radially outwardly which locate in catches of the circumferentially extending housing 6. During dispensing, the counter-rotation lock 7 rotates relative to the housing 6 and is therefore able to generate clicking noises. When the dose is being set or when the dose is being corrected, the counter-rotation lock is secured to the housing and does not therefore generate any clicking noises.

In addition to generating a noise during the clicking action, a tactile feedback may also be produced for a user.

In an alternative embodiment, the clicking mechanism is not disposed between the pendulum restrictor 8 and counter-rotation lock 7 and instead the pendulum restrictor 8 and counter-rotation lock 7 each have clicking elements, provided in the form of snapper arms biased radially outwardly which locate in catches of the housing 6. As a result, so-called "double clicks" can be generated during dispensing because in this instance both the pendulum restrictor 8 and counter-rotation lock 7 both rotate relative to the housing. When the dose is being set, only a "single click" is generated by the pendulum restrictor 8 because the counter-rotation lock 7 is secured to the housing.

In accordance with the present invention, including but not limited to the exemplary embodiments and exemplary preferred embodiments described herein, an injection device or dose setting device may independently incorporate other features, including the following features, either individually or in combination:

1. Step-down in ratio of the inward screwing movement of the dose setting sleeve 11 to the relatively shorter axial inward screwing movement of the threaded rod 9 during dispensing (both coupled in a rotationally locked arrangement).
2. Joint (same) rotation of the dose setting sleeve 11, coupling element 12, restrictor sleeve 8, counter-rotation lock (ratchet coupling) 7 and threaded rod 9 during dispensing.
3. Dose correction option based on a simple counter-rotation (inward turning or screwing) of the dose setting sleeve 11.
4. Restriction 300 due to the abutment of the restrictor nut 8 on the threaded rod 9 (producing or providing a pendulum movement of the restrictor nut 8).
5. Counter-rotation lock due to the ratchet coupling 7 (counter-rotation lock profiling in the housing 6 at least across the axial length of a maximum settable dose).
6. Restriction 60 due to a radial abutment of the dose setting sleeve 11 on the housing 6 (e.g. a threaded sleeve 10 secured to the housing).
7. Axial coupling of the counter-rotation lock 7 and pendulum restrictor 8 to prevent axial movement but permit a relative rotation (clicking when setting the dose).
8. No "dispensing clicks" generated by the "dose setting clicking elements" between the counter-rotation lock 7 and pendulum restrictor 6 (only by the counter-rotation lock 7 and housing 6).
9. Rotationally locked coupling between the threaded rod 9 and operating element 11 by coupling element 12 (and push knob 13) during dispensing.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising a dose setting device and an ampoule containing a substance, said dose setting device comprising:
 a restrictor element for restricting a maximum total of doses of the substance which can be set and dispensed from the ampoule, and
 an operating element for setting a dose by axial motion of the operating element extending in a proximal direction and which is coupled with the restrictor element so that the restrictor element moves during a dose setting movement of the operating element from an initial position inside the dose setting device toward a stop to block the movement of the restrictor element, thereby blocking the movement of the operating element in a dose setting direction and restricting the maximum total of doses set from the ampoule, wherein
 the restrictor element is coupled with the operating element so that the restrictor element moves relative to the dose setting device back to the initial position as the operating element undergoes a distal pushing-in movement by which the set dose is dispensed,
the injection device further comprising a threaded rod, wherein the threaded rod is mounted in the dose setting device or the injection device and is guided in an internal thread of the dose setting device or the injection device,
the dose setting device further comprising (a) a coupling for transmitting the distal pushing-in movement of the operating element to the threaded rod and (b) a counter-rotation lock for the threaded rod so that the threaded rod is able to move in only one direction relative to the dose setting device and a movement in the opposite direction of rotation is prevented, wherein
the counter-rotation lock is coupled to the restrictor element, such that the counter-rotation lock is prevented from moving axially but is rotatable relative to the restrictor element, and such that relative rotation generates clicking noises.

2. The injection device as claimed in claim 1, wherein the stop comprises at least one of an end of a thread of a threaded rod, an axial stop or a radial stop on the threaded rod, a housing or another structure of the dose setting device.

3. The injection device as claimed in claim 2, wherein the restrictor element is guided in a thread of the threaded rod.

4. The injection device as claimed in claim 2, wherein the restrictor element is locked to rotate in unison with the operating element or can be locked to rotate in unison with the operating element.

5. An injection device comprising a dose setting device, said dose setting device comprising:
 an operating element rotatable in a dose setting direction for setting a dose;
 a restrictor element rotatably engaged with and axially movable relative to the operating element, the restrictor element for restricting a maximum total of doses of a substance from an ampoule which can be set by the operating element;
 a threaded rod threadedly engaged with the restrictor element;
 a stop adapted to abut with the restrictor element upon the operating element rotatably engaging the restrictor element in the dose setting direction up to the maximum total of doses of the substance which can be set;
wherein:
 during dose setting by axial motion of the operating element extending in a proximal direction, the restrictor element is rotated by the operating element from an initial position along the threaded rod to a dose setting position;
 during dose delivery the operating element undergoes a distal pushing-in movement, by which the restrictor element and the operating element move axially relative to one another and the restrictor element slaves the threaded rod in axial distal movement as the restrictor element moves back to the initial position; and
 upon the restrictor element abutting the stop, the restrictor element is prevented from rotating along the threaded rod, thereby blocking movement of the operating element in the dose setting direction to restrict the maximum total of doses set from the ampoule.

6. The injection device as claimed in claim 5, wherein the stop comprises at least one of an end of a thread of the threaded rod, an axial stop or a radial stop on the threaded rod, a housing or another structure of the dose setting device.

7. The injection device as claimed in claim 6, wherein the restrictor element is guided in a thread of the threaded rod in a dose setting direction during dose setting.

8. The injection device as claimed in claim 7, wherein the operating element is further rotatable in a dose correcting direction for correcting a dose, and wherein the restrictor element rotatably engages with the operating element in the dose correcting direction.

9. The injection device as claimed in claim 5, wherein during dose setting and dose delivery, an axial displacement of the restrictor element differs from an axial displacement of the operating element.

10. The injection device as claimed in claim 5, further comprising a counter-rotation lock engaged with the threaded rod, said counter-rotation lock blocking axial movement of the threaded rod in one direction.

11. The injection device as claimed in claim 10, wherein the counter-rotation lock is coupled to and rotatable relative to the restrictor element, such that during the dose setting, relative rotation of the counter-rotation lock and the restrictor element generates clicking noises.

* * * * *